United States Patent
Jung et al.

(10) Patent No.: US 6,740,766 B2
(45) Date of Patent: May 25, 2004

(54) PREPARATION OF ORGANOCHLOROSILANES BY THE SILYLATION OF CONJUGATED DIENES WITH TRICHLOROSILANE

(75) Inventors: Il Nam Jung, Yongin-shi (KR); Bok Ryul Yoo, Koyang-shi (KR); Joon Soo Han, Sungnam-shi (KR); Seung-Hyun Kang, Seoul (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 10/385,538

(22) Filed: Mar. 11, 2003

(65) Prior Publication Data

US 2004/0063983 A1 Apr. 1, 2004

(30) Foreign Application Priority Data

Oct. 1, 2002 (KR) .................. 10-2002-0059872

(51) Int. Cl.$^7$ .................................................. C07F 7/08
(52) U.S. Cl. ...................................................... 556/406
(58) Field of Search .......................................... 556/406

(56) References Cited

U.S. PATENT DOCUMENTS 6,251,067 B1   6/2001   Strickholm
6,392,077 B1   5/2002   Jung et al.

OTHER PUBLICATIONS

Damrauer, Robert et al., Synthesis of 3–methylene–1, 1–dichlorosilacyclobutane and 1,1–dischlorosilacyclopent–3–ene, *Journal of Organometallic Chemistry*, 1990, pp. 7–12.

Chernyshev, E.A. et al., Silicon–Containing Heterocyclic Compounds XXX. Thermal Reactions of Dichlorosilylene with Unsaturated Compounds, *Translated from Zhurnal Obshchei Khimii*, Apr. 1978, vol. 48, No. 4, pp. 830–838.

Jung, Il Nam et al., Phosphonium Chloride–Induced Dichlorosilylene Generation from Trichlorosilane, XIII International Symposium on Organosilicon Chemistry, 35$^{th}$ Organosilicon Symposium held on Aug. 29, 2002.

*Primary Examiner*—Samuel Barts
(74) *Attorney, Agent, or Firm*—Jones Day

(57) ABSTRACT

The present invention relates to a process for preparing organosilicon compounds by the silylation of conjugated dienes and more particularly, to the process for preparing organosilicon compounds expressed by the following Formulas 1a and 1b in high yield, comprising the steps of heating trichlorosilane in the presence of quaternary organophosphonium salt catalystto generate dichlorosilylene (:SiCl$_2$); and silylating the result with linear or cyclic conjugated dienes,

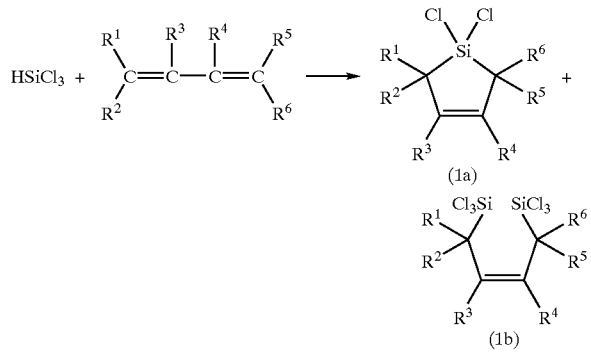

wherein $R^1$, $R^2$, $R^3$, $R^4$, $R^5$ and $R^6$ are independently a hydrogen atom, a $C_1$–$C_6$ alkyl, phenyl group, or two functional groups among $R^1$, $R^2$, $R^3$, $R^4$, $R^5$ and $R^6$ may be covalently bonded to each other to form a cyclic compound of $C_4$–$C_8$.

7 Claims, No Drawings

PREPARATION OF ORGANOCHLOROSILANES BY THE SILYLATION OF CONJUGATED DIENES WITH TRICHLOROSILANE

FIELD OF THE INVENTION

The present invention relates to a process for preparing organosilicon compounds by the silylation of conjugated dienes and more particularly, to the process for preparing organosilicon compounds expressed by the following formulas 1a and 1b in high yield, comprising the steps of heating trichlorosilane in the presence of quaternary organophosphonium salt catalyst to generate dichlorosilylene (:SiCl$_2$); and silylating the result with linear or cyclic conjugated dienes,

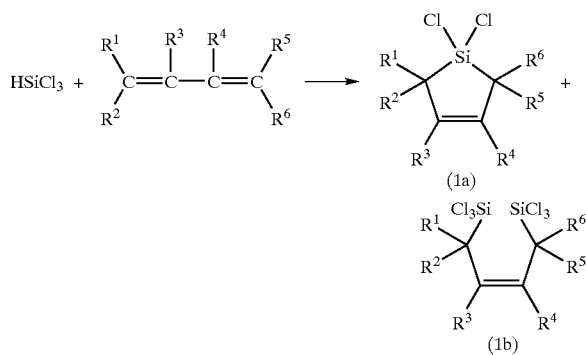

wherein $R^1$, $R^2$, $R^3$, $R^4$, $R^5$ and $R^6$ are independently a hydrogen atom, a $C_1$–$C_6$ alkyl or phenyl group, or two functional groups among $R^1$, $R^2$, $R^3$, $R^4$, $R^5$ and R6 may be covalently bonded to form a cyclic compound of $C_4$–$C_8$.

DESCRIPTION OF THE PRIOR ART

Organosilicon compounds have been widely used as useful starting materials for silicons. Especially, cyclic silicon compounds have become essential monomer precursors in the production of inorganic polymers by ring-opening polymerization. Further, they serve an important role in investigating the mechanisms of silicon chemistry. Therefore, researches in cyclic silicon compounds have been highly increased. By the 1980s, the only possible way of synthesizing the cyclic silicon compounds was through silylene (:Si). In 1978, Chernyshev of Russia reported the preparation of silylenes by the pyrolysis of hexachlorodisilane However, hexachlorodisilane is s are not suitable as a silylene precursors, because it would be too costly to be utilized on a large scale in industry [E. A. Chernyshev, N. G. Komalenkiva, S. A. Bashkirova and Sokolov, *Zh Obshch. Kihm.*, 1978, 48, 830]. Since then, extensive researches have been developed by Gaspar of the US. Alternative processes for preparing cyclic silicon compounds are taught by Weber of the US introducing a two-step process with the dichloro allylic compound as a starting material [Robert Damrauer, Roger Simonm Andre Laporterie, Georges Manuel, Young Tae Park and William P. Weber, *J. Organomet. Chem.*, 1990, 391, 7–12].

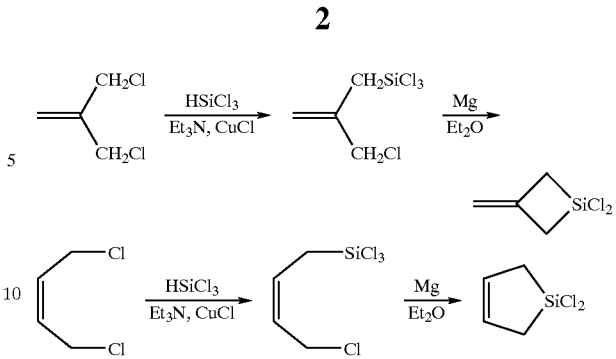

Although this method is still in use, it has some disadvantages that the reaction time is long; the isolation and purification are difficult; and this method is not applicable for other conjugated dienes.

The currently known methods for preparing cyclic silicon compounds are synthesizing mainly cyclic organic silanes by pyrolysis or photoreaction using costly disilanes at a high temperature or by using trichlorosilane and trialkylamine, followed by a Grignard reaction. However, these methods are not only limited in preparing a variety of cyclic silicon compounds, but also difficult to obtain good yield.

The present inventors have discovered a method of preparing a variety of organosilicon compounds by the dehydrohalogenation of alkyl halides and chlorosilanes in the presence of quaternary organophosphonium salt catalyst [U.S. Pat. Nos. 6,251,067 & 6,392,077]. It was noticed that a small amount of double silylated product was formed at the double bond of an allyl group with dehydrohologenation of allyl chloride or methyl allyl chloride. In the process of investigating the reaction condition to produce such double silylated product, we found that double silylation proceeds at the unsaturated organic compound due to the generation of silylene, when the reaction is carried at a higher temperature than that of the conventional dehydrohalogenation. The present invention was completed by identifying that cyclized organosilanes as a major product and double silylated compounds as a byproduct are obtained by the reaction of various conjugated dienes and silanes having Si—H bonds.

SUMMARY OF THE INVENTION

According to the above-mentioned prior arts, cyclic organosilicon compounds are prepared by the pyrolysis of conjugated dienes and disilanes at a high temperature, or by employing amines and simultaneous Grignard reaction. However, the coupling reaction between conjugated dienes and disilanes requires the use of costly disilanes which is further difficult to handle due to its instability, thus being inappropriate to be utilized for industrial purposes. Additionally, in the method employing amines, the ammonium salt is produced by the neutralization of hydrogen chloride generated during the reaction with amine, and in the Grignard reaction, a large amount of solvent has to be used, and the separation and treatment of the salt generated during the reaction with magnesium require a large cost.

Therefore, it would be also too costly to be utilized on a large scale in industry.

On the contrary, the process for preparing organosilicons according to this invention provides distinguished advantages: (1) the process is much more simple than that using the disilane compound; (2) trichlorosilane, which is much cheaper and industrially available, is used as a raw material; (3) the cyclic silicon compounds can be obtained with good yield because trichlorosilane can form dichlorosilylene (:SiCl$_2$) even at a low temperature in the presence of a small amount of quaternary organophosphonium salt; and (4) the catalyst can be easily recovered from the reaction medium and maintains good catalytic activity with recycles.

Accordingly, an object of this invention is to provide an economical and effective method for preparing organosilicon compounds.

DETAILED DESCRIPTION OF THE INVENTION

The present invention relates to a process for preparing the organosilicon compounds expressed by the following formulas 1a and 1b by the silylation of trichlorosilane (HSiCl$_3$) and conjugated diene organic compound expressed by the following formula 2 in the presence of quaternary organophosphonium salt catalyst,

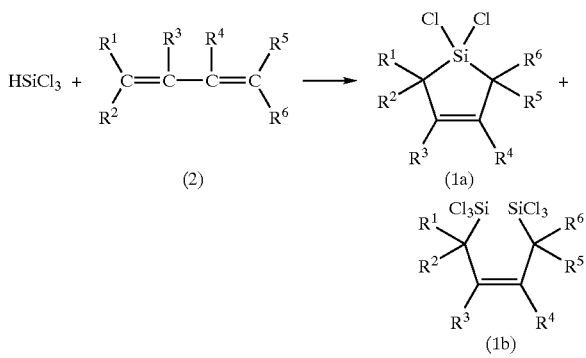

wherein R$^1$, R$^2$, R$^3$, R$^4$, R$^5$ and R$^6$ are independently a hydrogen atom, a C$_1$–C$_6$ alkyl or phenyl, or two functional groups among R$^1$, R$^2$, R$^3$, R$^4$, R$^5$ and R$^6$ may be covalently bonded to form a cyclic compound of C$_4$–C$_8$.

Hereunder is given a more detailed description.

This invention relates to a process for preparing the organosilicon compounds of formulas 1a and 1b by the silylation of trichlorosilanes and conjugated dienes with various structures in the presence of quaternary organophosphonium salt catalyst.

The process for preparing such various cyclic silicon compounds has never been reported before.

To improve disadvantages associated with the conventional processes, the inventors have directed to find effective catalysts which are economically feasible in the process for preparing organic silanes for a large scale in industry. So, the inventors used trichlorosilane as a starting material, which is relatively cheap, and a small amount of quaternary organophosphonium salt as a catalyst. The coupling reaction of the present invention is carried out at a temperature of 150–180° C. to give excellent yields. The catalyst could be easily recovered for recycle which makes the process more economical for industrial use.

The process for preparing organosilicon compounds by the silylation of conjugated dienes is described as follows.

First, trichlorosilane, conjugated dienes and quaternary organophosphonium salt are placed all together into a reaction tube which is stable at a high temperature and a high pressure (e.g., a stainless steel tube). After sealing the reaction tube with a stopper, heating and stirring may be applied to obtain organosilicon compounds of formulas 1a and 1b.

The conjugated dienes, raw material of this invention, can be expressed by the following formula 2,

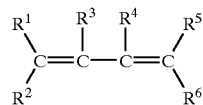

wherein R$^1$, R$^2$, R$^3$, R$^4$, R$^5$ and R$^6$ are the same as defined above.

Examples of the conjugated dienes of formula 2 include 1,3-butadiene, 2,3-dimethyl-1,3-butadiene, 2-methyl-1,3butadiene, 1,4diphenyl-1,3-butadiene, cyclopentadiene, cyclohexadiene, cycloheptadiene, cyclooctadiene and anthracene.

Quaternary organophosphonium salt, the catalyst of this invention, is effective in the silylation of conjugated dienes and trichlorosilane having a Si—H bond. Quaternary organophosphonium salt can be expressed by the following formula 3, $$(R')_4PX \qquad (3)$$

wherein X is a halogen atom; R' is independently C$_1$–C$_9$ alkyl, phenyl group, —(CH$_2$)$_n$—C$_6$H$_5$ (n is an integer of 0–6), or two R' can be covalently bonded to each other to form a cyclic compound of C$_4$–C$_8$.

Specific examples of the quaternary organophosphonium salt include benzyltributylphosphonium chloride, tetrabutylphosphonium chloride, tetrabutylphosphonium bromide, tetrabutylphosphonium iodide, tetramethylphosphonium bromide, tetraethylphosphonium chloride, (4-ethylbenzyl) triphenylphosphonium chloride, hexyltriphenylphosphonium chloride, benzyltriphenylphosphonium chloride and tetraphenylphosphonium chloride. The quaternary organophosphonium salt catalyst can be easily recovered from the reaction medium. For example, when the reaction product is placed under vacuum-distillation upon completion of the reaction, the remaining catalyst can be easily recovered. The recovery ratio can be as high as 80%. The recovered catalyst can be recrystallized from the solvent for recycle.

When the reaction mixture is heated in the presence of the quaternary organophosphonium salt catalyst, trichlorosilane is degraded to form dichlorosilylene (:SiCl$_2$) which reacts with conjugated dienes to give the organosilicon compounds expressed by formulas 1a and 1b. For 1 mol of conjugated dienes, 1–8 mol of trichlorosilane is used; and 0.01–1 mol, preferably 0.05–0.15 mol, of quaternary organophosphonium salt catalyst is used. There is no need to add a reaction solvent. If required, aromatic hydrocarbon may be used as the reaction solvent. The reaction is performed at 10–250° C., preferably at 100–200° C., for 1–48 hours. When the reaction is completed, the target compound can be obtained by distilling the reaction mixture under normal or reduced pressure.

As explained above, the present invention provides a method of preparing organosilicon compounds with good yield by the silylation of various conjugated dienes and trichlorosilanes having Si—H bonds in the presence of quaternary organophosphonium salt. This method uses a small amount of catalyst, which can be easily recovered for recycle and has good catalytic activity even at a low temperature. Considering these advantages, the present invention is a very economical and effective method, which can be used for the preparation of various and new organosilicon compounds. Furthermore, its process is very simple and the production cost is relatively low. The organosilicon compounds prepared by this invention can be widely used for the synthesis of various polymers.

The following examples are to be illustrative of the present invention. However, they should not be construed as limiting the scope of this invention.

EXAMPLE 1

Reaction of 1,3-Butadiene and Trichlorosilane

In a a 25 ml oven dried stainless steel tube ,1,3-butadiene (1.27 g, 23.26 mmol), trichlorosilane (14.7 g, 108.53 mmol) and tetrabutylphosphonium chloride (0.68 g, 2.31 mmol) were added under a dry nitrogen atmosphere. After sealing the cylinder with a cap, the reactor was maintained at 150° C. for 2 hours. The resulting mixture was distilled to yield 2.44 g (yield: 68%) of 1,1-dichlorosilacyclo-3-pentene main product, 0.88 g (yield: 20%) of crotyltrichlorosilane by product, and 0.37 g (yield: 5%) of trace 1,4-bis (trichlorosilyl)-2-butene.

1,1-Dichlorosilacyclo-3-pentene:

$^1$H-NMR(CDCl$_3$, ppm) 1.85(s, 4H, —Si—CH$_2$—), 5.98 (s, 2H, —CH=); $^{13}$C NMR(75 MHz, CDCl$_3$, ppm) 21.91, 129.12; MS(70 eV EI) m/z(relative intensity) 152(38), 118 (39), 116(100), 65(10), 63(25), 54(91), 53(15).

Crotyltrichlorosilane:

$^1$H-NMR(CDCl$_3$, ppm) δ1.64–1.66(d, 3H, —CH$_3$), 2.33–2.36(d, 2H, Cl$_3$Si—CH$_2$), 5.36–5.46(m, 1H, =CH—CH$_2$SiCl$_3$), 5.66–5.77(m, 1H, CH$_3$—CH=); $^{13}$C NMR(75 MHz, CDCl$_3$, ppm) δ12.98, 24.72, 118.58, 128.31; and MS(70 eV EI) m/z(relative intensity) 188(15),135(18), 133(18), 63(9), 55(100), 53(23)

1,4-Bis(trichlorosilyl)-2-butene:

MS(70 eV EI) m/z(relative intensity) 320(4), 191(35), 189(99), 187(100), 152(23), 151(3), 135(71), 133(70), 76(45), 63(24), 53(23).

EXAMPLE 2

Reaction of 2-Methyl-1,3-butadiene and Trichlorosilane

As in Example 1, 2-methyl-1,3-butadiene (1.00 g, 14.68 mmol), trichlorosilane (7.96 g, 58.77 mmol) and tetrabutylphosphonium chloride (0.43 g, 1.46 mmol) were added in a 25 mL stainless steel tube under nitrogen atmosphere. After sealing the cylinder with a cap, the reactor was maintained at 150° C. for 5 hours. The resulting mixture was distilled to yield 2.31 g (94%) of 3-methyl-1,1-dichlorosilacyclo-3-pentene main product.

3-Methyl-1,1-dichlorosilacyclo-3-pentene:

$^1$H-NMR(CDCl$_3$, ppm) δ1.79(s, 2H, —Si—CH$_2$—CCH$_3$=), 1.81(s, 3H, —CH$_3$), 1.88(s, 2H, —Si—CH$_2$—CH=), 5.59–5.61(t, 1H, —CH$_2$—CH=);

$^{13}$C NMR(75 MHz, CDCl$_3$, ppm) δ23.10, 23.74, 27.00, 123.03, 138.73; and

MS(70 eV EI) m/z(relative intensity) 166(55), 151(11), 138(17), 130(99), 68(100), 67(70), 65(16), 63(30), 53(22).

EXAMPLE 3

Reaction of 2-Methyl-1,3-butadiene and Trichlorosilane

As in Example 1, 2-methyl-1,3-butadiene (1.00 g, 14.68 mmol), trichlorosilane (7.94 g, 58.62 mmol) and benzyltributylphosphonium chloride (0.56 g, 1.44 mmol) were added in a 25 mL stainless steel tube under nitrogen atmosphere. After sealing the cylinder with a cap, the reactor was maintained at 150° C. for 5 hours. The resulting mixture was distilled to yield 2.16 g (yield: 88%) of 3-methyl-1,1-dichlorosilacyclo-3-pentene.

EXAMPLE 4

Reaction of 2-Methyl-1,3-butadiene and Trichlorosilane

As in Example 1, 2-methyl-1,3butadiene (1.01 g, 14.83 mmol), trichlorosilane (7.99 g, 58.99 mmol) and tetrabutylphosphonium bromide (0.50 g, 1.47 mmol) were added in a 25 mL stainless steel tube under nitrogen atmosphere. After sealing the cylinder with a cap, the reactor was maintained at 150° C. for 5 hours. The resulting mixture was distilled to yield 2.19 g (yield: 89%) of 3-methyl-1,1-dichlorosilacyclo-3-pentene main product.

EXAMPLE 5

Reaction of 2,4-Hexadiene and Trichlorosilane

As in Example 1, 1,3-hexadiene (1.00 g, 12.17 mmol), trichlorosilane (6.59 g, 48.65 mmol) and tetrabutylphosphonium chloride (0.36 g, 1.22 mmol) were added in a 25 mL stainless steel tube under nitrogen atmosphere. After sealing the cylinder with a cap, the reactor was maintained at 180° C. for 8 hours. The resulting mixture was distilled to yield 1.64 g (yield: 74%) of 1,1-dichloro-2,5-dimethylsilacyclo-3-pentene and 0.43 g (yield: 10%) of 2,5-bis(trichlorosilyl)-3-hexene main products.

1,1-Dichloro-2,5-dimethyl-silacyclo-3-pentene:

$^1$H-NMR(CDCl$_3$, ppm) δ1.15–1.18(d, 6H, —Si—CHCH$_3$—), 1.98–2.01(q, 2H, —Si—CHCH$_3$—), 5.80(s, 2H, —CH$_2$—CH=);

$^{13}$C NMR(75 MHz, CDCl$_3$, ppm) δ14.84, 27.23, 134.80; and

MS(70 eV EI) m/z(relative intensity) 180(23), 99(4), 82(100), 67(65), 63(12), 54(7).

2,5-Bis(trichlorosilyl)-3-hexene:

MS(70 eV EI) m/z(relative intensity) 348(5), 219(36), 217(99), 215(100), 189(14), 179(16),137916), 135(33), 133 (34), 81(35), 67(16), 55(17).

EXAMPLE 6

Reaction of 2,4-Hexadiene and Trichlorosilane

As in Example 1, 1,3-hexadiene (0.99 g, 12.06 mmol), trichlorosilane (6.60 g, 48.73 mmol) and tetrabutylphosphonium iodide (0.47 g, 1.22 mmol) were added in a 25 mL stainless steel tube under nitrogen atmosphere. After sealing the cylinder with a cap, the reactor was maintained at 180 ° C. for 10 hours. The resulting mixture was distilled to yield 1.32 g (yield: 60%) of 1,1-dichloro-2,5-dimethyl-silacyclo-3-pentene and 0.43 g (yield: 10%) of 2,5-bis(trichlorosilyl)-3-hexene main products.

EXAMPLE 7

Reaction of 2,3-Dimethyl-1,3-butadiene and Trichlorosilane

As in Example 1, 2,3-dimethyl-1,3-butadiene (1.00 g, 12.17 mmol), trichlorosilane (6.61 g, 48.80 mmol) and tetrabutylphosphonium chloride (0.36 g, 1.22 mmol) were added in a 25 mL stainless steel tube under nitrogen atmosphere. After sealing the cylinder with a cap, the reactor was maintained at 150° C. for 5 hours. The resulting mixture was distilled to yield 2.03 g (yield: 92%) of 3,4-dimethyl-1,1-dichlorosilacyclo-3-pentene main product.

3,4-Dimethyl-1,1-dichlorosilacyclo-3-pentene:

$^1$H-NMR(CDCl$_3$, ppm) δ1.75(s, 6H, =CCH$_3$),1.87(s, 4H, —Si—CH$_2$—CH=);

$^{13}$C NMR(75 MHz, CDCl$_3$, ppm) δ19.19, 29.59, 129.72; and

MS(70 eV EI) m/z(relative intensity) 180(66), 167(37), 165(54), 144(39), 129(39), 82(64(67(1000, 65(21), 63(37).

EXAMPLE 8

Reaction of 2,3-Dimethyl-1,3-butadiene and trichlorosilane

As in Example 1, 2,3-dimethyl-1,3-butadiene (1.00 g, 12.17 mmol), trichlorosilane (6.59 g, 48.65 mmol) and tetraphenylphosphonium chloride (0.46 g, 1.23 mmol) were added in a 25 mL stainless steel tube under nitrogen atmosphere. After sealing the cylinder with a cap, the reactor was maintained at 150° C. for 8 hours. The resulting mixture was distilled to yield 1.79 g (yield: 81%) of 3,4-dimethyl-1,1-dichlorosilacyclo-3-pentene.

EXAMPLE 9

Reaction of 2,3-Dimethyl-1,3-butadiene and Trichlorosilane

As in Example 1, 2,3-dimethyl-1,3-butadiene (1.02 g, 12.42 mmol), trichlorosilane (6.63 g, 48.95 mmol) and tetramethylphosphonium bromide (0.21 g, 1.23 mmol) were added in a 25 mL stainless steel tube under nitrogen atmosphere. After sealing the cylinder with a cap, the reactor was maintained at 150° C. for 5 hours. The resulting mixture was distilled to yield 2.03 g (yield: 90%) of 3,4-dimethyl-1,1-dichlorosilacyclo-3pentene main product.

EXAMPLE 10

Reaction of 2,3-Dimethyl-1,3-butadiene and Trichlorosilane

As in Example 1, 2,3-dimethyl-1,3-butadiene (1.00 g, 12.17 mmol), trichlorosilane (6.60 g, 48.72 mmol) and tetraethylphosphonium chloride (0.22 g, 1.20 mmol) were added in a 25 mL stainless steel tube under nitrogen atmosphere. After sealing the cylinder with a cap, the reactor was maintained at 150° C. for 5 hours. The resulting mixture was distilled to yield 2.00 g (yield: 89%) of 3,4-dimethyl-1,1-dichlorosilacyclo-3pentene main product.

EXAMPLE 11

Reaction of 2,3-Dimethyl-1,3-butadiene and Trichlorosilane

As in Example 1, 2,3-dimethyl-1,3-butadiene (1.00 g, 12.17 mmol), trichlorosilane (6.61 g, 48.00 mmol) and benzyltriphenylphosphonium chloride (0.47 g, 1.21 mmol) were added in a 25 mL stainless steel tube under nitrogen atmosphere. After sealing the cylinder with a cap, the reactor was maintained at 150° C. for 8 hours. The resulting mixture was distilled to yield 1.75 g (yield: 78%) of 3,4dimethyl-1,1-dichlorosilacyclo-3pentene main product.

EXAMPLE 12

Reaction of 1,4-Diphenyl-1,3-butadiene and Trichlorosilane

As in Example 1, 1,4-diphenyl-1,3-butadiene (2.00 g, 9.70 mmol), trichlorosilane (5.25 g, 38.76 mmol), tetrabutylphosphonium chloride (0.29 g, 0.98 mmol) and 5 mL of toluene (solvent) were added in a 25 mL stainless steel tube under nitrogen atmosphere. After sealing the cylinder with a cap, the reactor was maintained at 180° C. for 8 hours. After removing the solvent and unreacted trichlorosilane and tetrachlorosilane through simple distillation, this reaction mixture was distilled under reduced pressure to separate the catalyst and the product. The product was recrystallized from 10 mL of n-hexane for 4 days to yield 1.51 g (yield: 51%) of 2,5-diphenyl-1,1-dichlorosilacyclo-3-pentene and 1.20 g (yield: 26%) of 1,4-bis(trichlorosilyl)-1,4-diphenyl-2-butene.

2,5-Diphenyl-1,1-dichlorosilacyclo-3-pentene:

$^1$H-NMR(CDCl$_3$, ppm) δ3.69(s, 2H, —Si—CHPh—), 1.81(s, 3H, —CH$_3$), 6.33(s, 2H, —CH=), 7.19–7.39(m, 10H, —CHPh—);

$^{13}$C NMR(75 MHz, CDCl$_3$, ppm) δ41.79, 126.02, 127.33, 128.61, 133.44, 138.20; and MS(70 eV EI) m/z(relative intensity) 304(41), 206(100), 205(35), 203(16), 191(27), 19(27), 128(39), 115(15), 91(61), 89(14), 77(10), 63(9).

1,4-Bis(trichlorosilyl)-1,4-diphenyl-2-butene:

MS(70 eV EI) m/z(relative intensity) 339(7, —SiCl$_3$), 261(10), 251(44), 249(44), 227(17), 225(32), 223(19), 203 (14), 135(15), 133(15), 115(24), 91(100).

EXAMPLE 13

Reaction of 2,3-diphenyl-1,3-butadiene and Trichlorosilane

As in Example 1, 2,3-diphenyl-1,3-butadiene (2.00 g, 9.70 mmol), trichlorosilane (5.23 g, 38.61 mmol), tetrabutylphosphonium chloride (0.29 g, 0.98 mmol) and 5 mL of toluene (solvent) were added in a 25 mL stainless steel tube under nitrogen atmosphere. After sealing the cylinder with a cap, the reactor was maintained at 150° C. for 5 hours. After removing the solvent and unreacted trichlorosilane and tetrachlorosilane through simple distillation, this reaction mixture was distilled under reduced pressure to separate the catalyst and the product. The product was recrystallized from 10 mL of n-hexane for 2 days to yield 2.66 g (yield: 90%) of 3,4-diphenyl-1,1-dichlorosilacyclo-3-pentene.

3,4-Diphenyl-1,1-dichlorosilacyclo-3-pentene:

$^1$H-NMR(CDCl$_3$, ppm) δ2.52(s, 4H, —Si—CH$_2$—), 7.04–7.17(m, 10H, —CH$_2$—CPh=);

$^{13}$C NMR(75 MHz, CDCl$_3$, ppm) δ30.18, 126.82, 127.97, 128.67, 136.08, 140.49; and MS(70 eV EI) m/z(relative intensity) 304(87), 267(17), 205(38), 203(20), 191(100), 165(14), 128(25), 91(23), 77(14), 63(10).

EXAMPLE 14

Reaction of 2,-Diphenyl-13-butadiene and Trichlorosilane

As in Example 1, 2,3-diphenyl-1,3-butadiene (2.01 g, 9.74 mmol), trichlorosilane (5.25 g, 38.76 mmol), 4-(ethyl) triphenylbutylphosphonium chloride (0.41 g, 0.98 mmol) and 5 mL of toluene (solvent) were added in a 25 mL stainless steel tube under nitrogen atmosphere. After sealing the cylinder with a cap, the reactor was maintained at 150° C. for 10 hours. After removing the solvent and unreacted trichlorosilane and tetrachlorosilane through simple distillation, this reaction mixture was distilled under reduced pressure to separate the catalyst and the product. The product was recrystallized from 10 mL of n-hexane for 2 days to yield 2.46 g (yield: 83%) of 3,4-diphenyl-1,1-dichlorosilacyclo-3-pentene.

EXAMPLE 15

Reaction of 2,3-Diphenyl-1,3-butadiene and Trichlorosilane

As in Example 1, 2,3-diphenyl-1,3-butadiene (2.00 g, 9.70 mmol), trichlorosilane (5.22 g, 38.54 mmol), hexyltriphenylphosphonium bromide (0.41 g, 0.96 mmol) and 5 mL of toluene (solvent) were added in a 25 mL stainless steel tube under nitrogen atmosphere. After sealing the cylinder with a cap, the reactor was maintained at 150° C. for 10 hours. After removing the solvent and unreacted trichlorosilane and tetrachlorosilane through simple distillation, this reaction mixture was distilled under reduced pressure to separate the catalyst and the product. The product was recrystallized from 10 mL of n-hexane for 2 days to yield 2.28 g (yield: 77%) of 3,4-diphenyl-1,1-dichlorosilacyclo-3-pentene.

EXAMPLE 16

Reaction of 1,3-Cyclopentadiene and Trichlorosilane

As in Example 1, 1,3-cyclopentadiene (1.00 g, 15.13 mmol), trichlorosilane (8.19 g, 60.47 mmol) and tetrabutylphosphonium chloride (0.44 g, 1.49 mmol) were added in a 25 mL stainless steel tube under nitrogen atmosphere. After sealing the cylinder with a cap, the reactor was maintained at 180° C. for 10 hours. The resulting mixture was distilled to yield 0.45 g (yield: 9%) of 2,4-bis(trichlorosilyl)-1-pentene.

2,4-Bis(trichlorosilyl)-1-pentene:

MS(70 eV EI) m/z(relative intensity) 332(4), 202(35), 201(100), 199(100), 165(45), 163(66), 135(43), 133(43), 65(20), 63(19).

EXAMPLE 17

Reaction of 1,3-Cyclohexadiene and Trichlorosilane

As in Example 1, 1,3-cyclohexadiene (0.98 g, 12.23 mmol), trichlorosilane (6.63 g, 48.95 mmol) and tetrabutylphosphonium chloride (0.35 g, 1.19 mmol) were added in a 25 mL stainless steel tube under nitrogen atmosphere. After sealing the cylinder with a cap, the reactor was maintained at 180° C. for 12 hours. The resulting mixture was distilled to yield 1.92 g (yield: 45%) of 2,6-bis(trichlorosilyl)-1-hexene.

2,6-Bis(trichlorosilyl)-1-hexene:

MS(70 eV EI) m/z(relative intensity) 346(3), 217(35), 215(99), 213(100), 179(21), 177(32), 135(33), 133(33), 79(76), 77(31),63(12), 51910).

EXAMPLE 18

Reaction of 1,3-Cycloheptadiene and Trichlorosilane

As in Example 1, 1,3-cycloheptadiene (1.00 g, 10.62 mmol), trichlorosilane (5.76 g, 42.52 mmol) and tetrabutylphosphonium chloride (0.31 g, 1.05 mmol) were added in a 25 mL stainless steel tube under nitrogen atmosphere. After sealing the cylinder with a cap, the reactor was maintained at 180° C. for 18 hours. The resulting mixture was distilled to yield 0.96 g (yield: 25%) of 2,6-bis(trichlorosilyl)-1-heptene.

2,6-Bis(trichlorosilyl)-1-heptene:

MS(70 eV EI) m/z(relative intensity) 231(37), 229(100), 227(99), 191(17), 135(28), 133(28), 93(37), 91(18), 79(14), 77(15),65(12).

EXAMPLE 19

Reaction of 1,3-Cyclooctadiene and Trichlorosilane

As in Example 1, 1,3-cyclooctadiene (1.00 g, 9.24 mmol), trichlorosilane (5.01 g, 36.99 mmol) and tetrabutylphosphonium chloride (0.27 g, 0.92 mmol) were added in a 25 mL stainless steel tube under nitrogen atmosphere. After sealing the cylinder with a cap, the reactor was maintained at 180° C. for 20 hours. The resulting mixture was distilled to yield 0.35 g (yield: 10%) of 2,7-bis(trichlorosilyl)-1-octene.

2,7-Bis(trichlorosilyl)-1-octene:

MS(70 eV EI) m/z(relative intensity) 374(3), 245(31), 243(85), 241(86), 215(18), 213(18), 201(30), 199(28), 137(25), 135(57), 133(57), 81(66), 79(45), 67(100).

EXAMPLE 20

Reaction of Anthracene and Trichlorosilane

As in Example 1, anthracene (1.00 g, 5.61 mmol) trichlorosilane (22.44 g, 38.61 mmol), tetrabutylphosphonium chloride (0.17 g, 0.57 mmol) and 5 mL of benzene (solvent) were added in a 25 mL stainless steel tube under nitrogen atmosphere. After sealing the cylinder with a cap, the reactor was maintained at 180° C. for 5 hours. After removing the solvent and unreacted trichlorosilane and tetrachlorosilane through simple distillation, this reaction mixture was distilled under reduced pressure to separate the catalyst and the product. The product was recrystallized from 5 mL of toluene for 2 days to yield 0.5 g (yield: 20%) of 9.10-bis(trichlorosilyl)-9,10-dihydroanthracene.

9,10-Bis(trichlorosilyl)-9,10-dihydroanthracene:

MS(70 eV EI) m/z(relative intensity) 446(2), 315(28), 313(72), 311(71), 178(100), 151(9), 135(6), 133(6).

As explained above, the present invention provides a process for the preparation of organosilicon compounds expressed by formulas 1a and 1b by heating quaternary organophosphonium salt catalyst and trichlorosilane to generate dichlorosilylene (:SiCl$_2$) and reacting it with linear chain or cyclic conjugated dienes. This invention uses a smaller amount of catalyst compared to the conventional preparing methods. The catalyst can be easily recovered for recycle. Also, the silylation agent, trichlorosilane (HSiCl$_3$), is an easily available material in the industry. Therefore, this invention is effective in preparing organosilicon compounds industrially, which are used for silicon polymers or crosslinking agents. Accordingly, this invention is effective for industrial mass production of organosilicon compounds, which are widely used for raw material of silicon polymers, silane adhesives, etc.

What is claimed is:

1. A process for preparing organosilicon compounds of formulas 1a and 1b by the silylation of trichlorosilane (HSiCl$_3$) and conjugated dienes of formula 2 in the presence of quaternary organophosphonium salt catalyst,

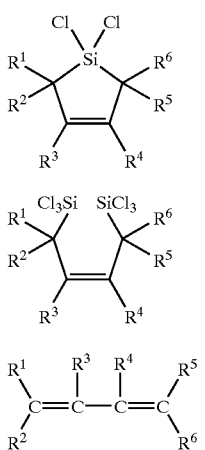

wherein $R^1$, $R^2$, $R^3$, $R^4$, $R^5$ and $R^6$ are independently a hydrogen atom, a $C_1$–$C_6$ alkyl, or phenyl group; or two functional groups among $R^1$, $R^2$, $R^3$, $R^4$, $R^5$ and $R^6$ are covalently bonded to each other to form a cyclic compound of $C_4$–$C_8$.

2. The process for preparing organosilicon compounds according to claim 1, wherein 1–8 mols of trichlorosilane are used for 1 mol of conjugated dienes.

3. The process for preparing organosilicon compounds according to claim 1, wherein said quaternary phosphonium salt is expressed by the following formula (3)

$$(R')_4 PX \tag{3}$$

wherein X is a halogen atom; R' is independently $C_1$–$C_9$ alkyl or phenyl group, —$(CH_2)_n$—$C_6H_5$ (n is an integer of 0–6), or two R' can be covalently bonded to each other to form a cyclic compound of $C_4$–$C_8$.

4. The process for preparing organosilicon compounds according to claim 1, wherein 0.01–1 mol of said catalyst is used for 1 mol of conjugated dienes.

5. The process for preparing organosilicon compounds according to claim 4, wherein 0.05–0.15 mol of said catalyst is used for 1 mol of conjugated dienes.

6. The process for preparing organosilicon compounds according to claim 1, wherein said silylation is performed at a temperature of 10–250° C.

7. The process for preparing organosilicon compounds according to any one of claims 1–6, wherein said silylation is performed without use of a reaction solvent or in the presence of an aromatic hydrocarbon solvent.

* * * * *